United States Patent [19]

Maes

[11] Patent Number: 4,965,192
[45] Date of Patent: * Oct. 23, 1990

[54] A60-ANTIGEN FROM MYCOBACTERIA AND USE THEREOF AS TUBERCULIN AND AS VACCINE

[75] Inventor: Roland F. Maes, Mutzig, France

[73] Assignee: Anda Biologicals, Mutzig, France

[ * ] Notice: The portion of the term of this patent subsequent to Oct. 11, 2005 has been disclaimed.

[21] Appl. No.: 187,919

[22] Filed: Apr. 29, 1988

Related U.S. Application Data

[63] Continuation-in-part of Ser. No. 678,470, Dec. 5, 1984, Pat. No. 4,777,130.

[51] Int. Cl.$^5$ ............... G01N 33/53; G01N 35/566; C12Q 1/00; A61K 39/40
[52] U.S. Cl. .................................... 435/7; 435/4; 435/863; 435/864; 436/501; 436/811; 436/815; 530/806; 530/820; 530/825; 424/87; 424/92
[58] Field of Search ............ 436/501, 811, 815; 435/4, 7, 863, 864; 530/806, 820, 825; 424/9, 87, 92

[56] References Cited

U.S. PATENT DOCUMENTS

| | | | |
|---|---|---|---|
| 4,410,660 | 10/1983 | Straus | 424/87 X |
| 4,591,552 | 5/1986 | Neurath | 436/534 X |
| 4,777,130 | 10/1988 | Maes | 436/501 X |

*Primary Examiner*—Jack Spiegel
*Attorney, Agent, or Firm*—William J. Daniel

[57] ABSTRACT

An interspecific antigen of Mycobacteria consists essentially of a mixture in substantially immunochemically pure form of a protein having a molecular weight of at least about $4 \times 10^6$ Daltons and polysaccharide having a molecular weight of at least about $1 \times 10^6$ Daltons, and has when subjected to cross-electrophoresis an immunoelectrophoretic precipitation pattern corresponding to A60-antigen of Mycobacteria bovis strain BCG. This antigen is effective for detecting the prior exposure of a subject to Mycobacterial infections by a cutaneous test.

4 Claims, 3 Drawing Sheets

A60-ANTIGEN FROM MYCOBACTERIA AND USE THEREOF AS TUBERCULIN AND AS VACCINE

This application is a continuation-in-part of application Ser. No. 678,470, filed Dec. 5, 1984 now U.S. Pat. No. 4,777,130.

FIELD OF THE INVENTION

This invention relates to an antigen derived from Mycobacteria and is concerned more particularly with an interspecific antigen of Mycobacteria exhibiting upon cross-electrophoresis an immunoelectrophoretic precipitation pattern corresponding to A60 antigen of *Mycobacteria bovis* strain BCG and to the use of such A60 antigen as a challenge antigen for indicating cell-medicated immunity by delayed hypersensitive reaction.

BACKGROUND OF THE INVENTION

It is known that the detection of delayed sensitivity reactions which are the basis for cutaneous testing for tuberculosis can be accomplished by a material extracted from *Mycobacterium bovis*, strain BCG (Bacillus Calmette-Guerin). This BCG derived material, as well as so-called old tuberculin (O.T.) and Purified PROTEIN Derivative (PPD) are heterogeneous in composition. There is, consequently, a need for a purer and more precisely characterized antigenic material, possessing greater and more reliable effectiveness for the cutaneous testing for such diseases.

It was found that a high molecular weight antigenic material related in important immunochemical respects to the A60 antigen of *M. bovis* strain BCG may be extracted from various Mycobacterial species in substantially immunochemically pure form by the method claimed in U.S. patent application No. 678,170, filed Dec. 5, 1984. This antigenic material proved to possess those properties required to serve as the capture antigen in diagnostic test procedures and resulted in the development of an effective serological diagnostic test also claimed in that application. Taking advantage of the refined and reliable detection test thus made available, it has now been established that the A60 like antigenic material in question can be effectively used as the challenge antigen in delayed sensitivity tests for confirming the acquisition of immunity upon vaccination as well as prior exposure of the subject to tubercular-related infections.

SUMMARY OF THE INVENTION

The high molecular weight A60 is capable of eliciting as a delayed hypersensitivity as a cellular immune response and also able to serve as a challenge antigen when administered in much smaller amounts for indicating or revealing an established hypersensitivity either artificially or naturally initiated. This antigen has the potential for replacing the currently used tubercular-derived materials as a sensitizing agent, or challenge antigen, used in cutaneous testing for such diseases.

ISOLATION OF THE A60 ANTIGENS

A number of different strains of Mycobacteria were used for the isolation of A60 antigen and were obtained mainly from the National Collection of Cultures of Microorganisms, C.N.C.M., Pasteur Institute, 25, rue du Docteur Roux, 75724 Paris FRANCE. Another source was the Station experimentale d'aviculture B.P. 9, 22440 PLOUFSAGAN, FRANCE.

The bacterial (with the exception of *M. leprae*) are multiplied in Dubos medium supplemented with 5% horse serum decomplemented through heating at 56° C. during 30'. They are collected at the end of the growth phase through centrifugation and the bacterial walls are disrupted by compression and decompression in a French cell (Aminco instruments, Silver Spring, Md., U.S.A.) at 8000 p.s.i. and 4° C.

Figure 1:
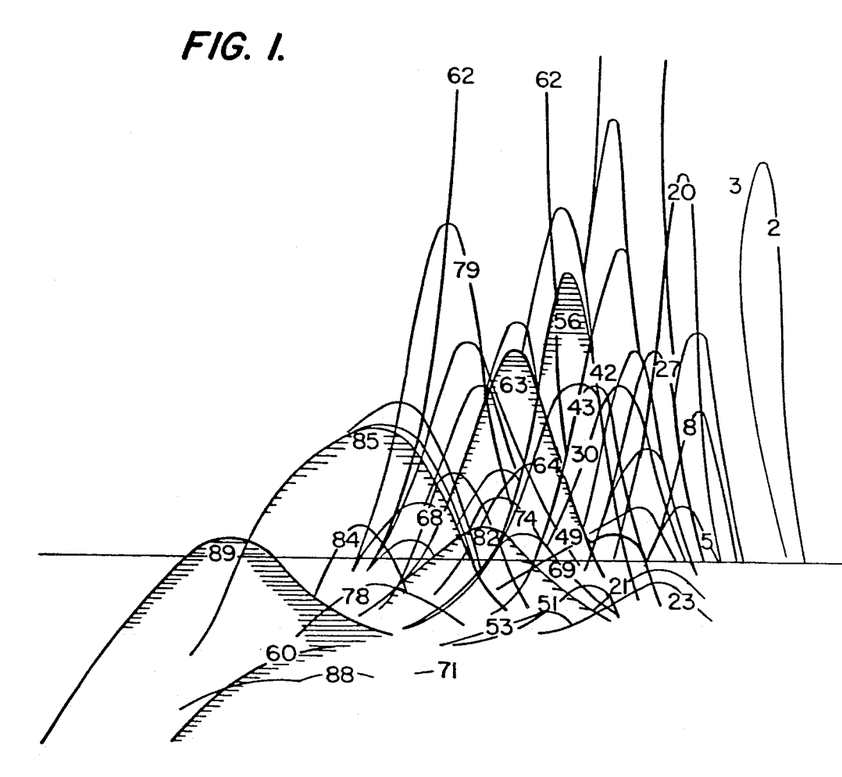
FIG. 1 is an illustration of the reference system (Closs et al, Scand. J. Immunol., 1980, 12, 249–263) for extracellular antigens of *M. bovis* BCG obtained by bidimensional immunoelectrophoresis and colored with Coomassie blue, the second dimension occurring through a gel containing whole anti-BCG serum.
Figure 2:
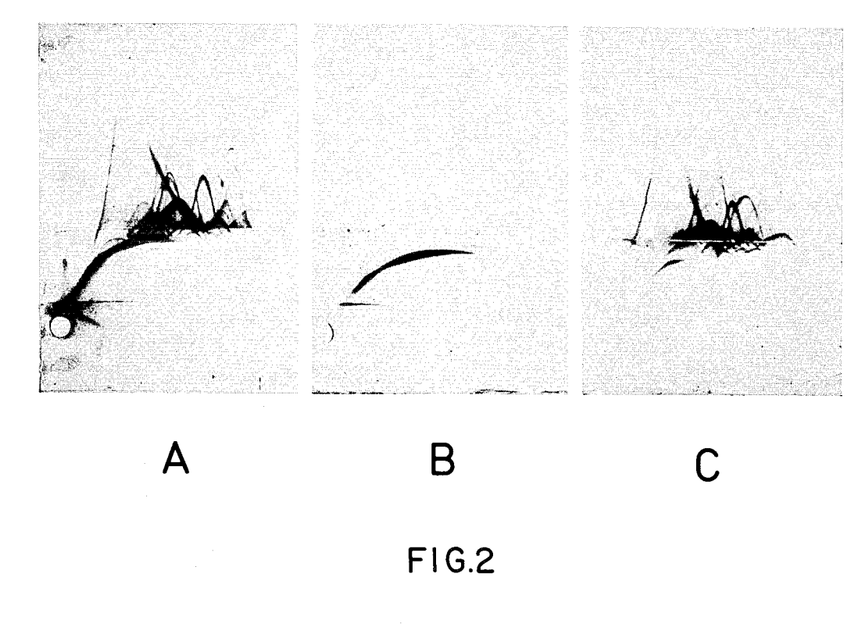
FIG. 2 shows the immunoelectrophoretic patterns resulting from exclusion chromatography of a cytoplasmic sample of *M. bovis* BCG in which A is the starting cytoplasma, B is an exclusion peak constituted substantially entirely of A60-like antigen, and C is the inclusion peak containing all other proteinaceous matter.
Figure 3:
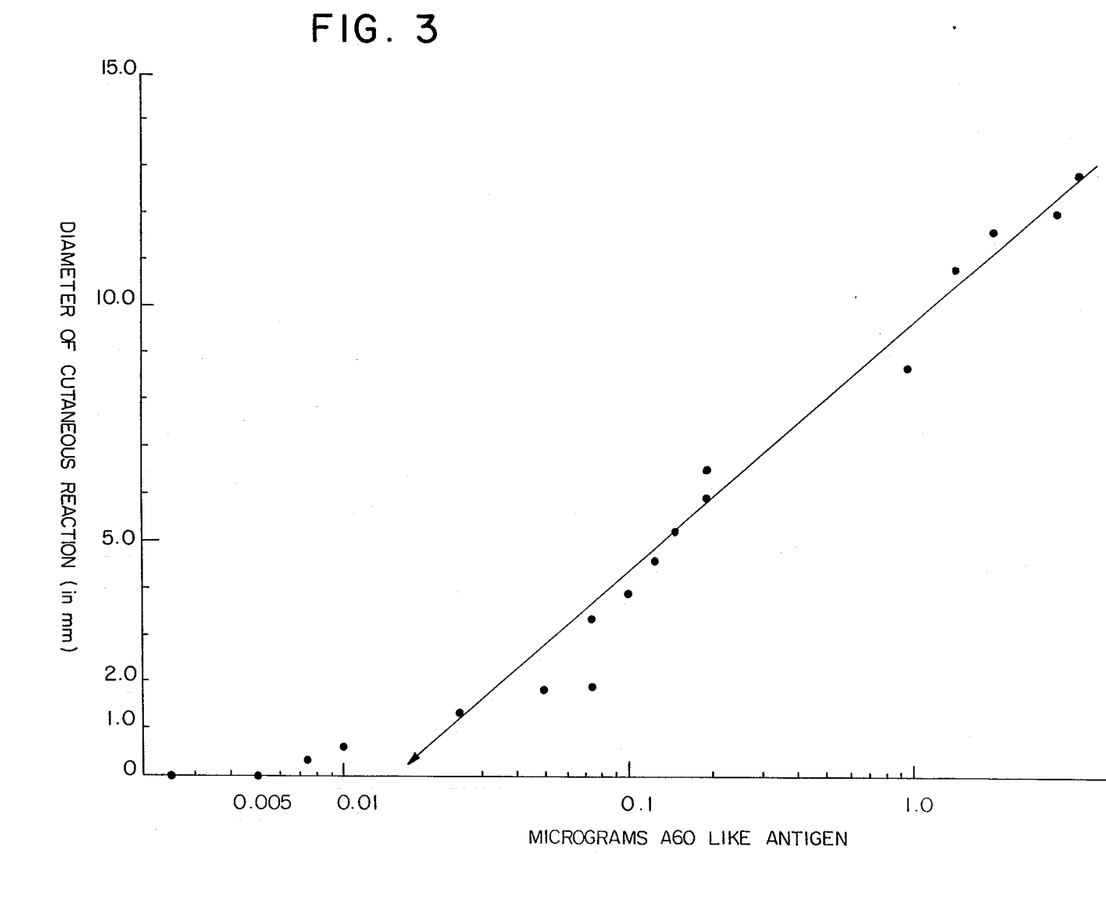
FIG. 3 is a plot of the degrees of cutaneous reaction, measured by the observed diameters in mm of the swollen areas, resulting from the injection as challenge antigen of varying amounts, expressed in micrograms of the A60 antigen in test guinea pigs pre-sensitized with killed *M. bovis* bacteria, from which the minimum level of the antigen capable of eliciting a perceivable reaction can be seen.

A60 antigen from various Mycobacteria is easily isolated and purified in a one-step chromatographic procedure. Homogenates of the various Mycobacteria are centrifuged at 20000 r.p.m. for 10! at 4° C. to eliminate cellular debris from the supernatant containing the cytoplasm. When a cytoplasmic sample of *M. bovis* BCG is subjected to bidimensional or cross immunoelectrophoresis (CIE), the various antigenic constituents thereof are fractionated in a pattern as illustrated in FIG. 1. Specifically, the reference pattern of FIG. 1 is obtained by subjecting a test sample, about 24 µl of the starting cytoplasmic sample in 10 µl barbital buffer, to electrophoresis in two directions or dimensions with the second direction of electrophoresis being through an agarose gel containing whole anti-BCG serum obtained commercially from Dako of Denmark, and then to coloring by Coomassie blue. FIG. 2 shows the result of molecular sieve chromagraphy obtained by passing a cytoplasmic sample of *M. bovis* BCG consisting of 16.5 mg protein in 1 ml on a Sepharose 6B column (Trademark for spherical agarose gel beads with exclusion limits of about $4 \times 10^6$ daltons for proteins and $1 \times 10^6$ daltons for polysaccharides sold by Pharmacia Fine Chemicals AB). The starting sample is indicated at A and has a proteinic pattern of immunoelectrophoresis similar to that of FIG. 1; the exclusion peak is indicated at B which consists substantially of A60 antigen as shown by its immunoelectrophoretic location, and the inclusion peak is at C which includes all other proteinaceous matter, i.e., all other antigens present in the sample. If desired, peak B, in case the presence of some contaminants is still observed after immunoelectrophoretic analysis may be re-chromatographed on the same column, which will yield A60 antigen in an immunochemically homogeneous form.

A60 antigen purified by bichromatography on a Sepharose 6B column has been chemically analyzed. It is composed of 57% protein and 43% polysaccharides. Its unit of reference was established as follows: 1 unit A60 antigen is the quantity of electrophoretically purified and Coomassie blue colored antigen whose absorbance in solution at 530 nm is:

$$A_{530}^{1 cm} = 0.1$$

This spectrophotometric unit corresponds to 1.5 µg of the proteinic component and to 1.23 µg of the polysaccharidic component. It corresponds thus to 2.45 µg of cytoplasmic A60 antigen.

Antigen A60 of *M. bovis* is the slowest migrating component of the bacterial cytoplasm into the electrophoretic field under the following test conditions (1% agarose in Tris-barbital buffer 0.02M at pH 8.6; 8 volts/cm during 1 h at 15° C. in the first dimension and 3 volts/cm during 18 h at 15° C. in the second dimension; detection of the proteinic components by Coomassie blue). The bulk of the work was accomplished with *M. bovis* attenuated strain-Calmette-Guerin Bacillus (BCG). After having determined the optimal conditions for isolation of A60 antigen, similar materials, recognized by a characteristic immunoelectrophoretic pattern corresponding to the A60 antigen of *M. bovis* strain BCG were isolated, through the same simple molecular-sieve chromatographic technique, from a photochromogen (group I, *M. kansasii*), a scotochromogen (group II, *M. scrofulaceum*), a nonchromogen (group III, *M. xenopi*) and a "rapid grower" (group IV, *M. chelonei*). To these representatives of the various Mycobacterial groups that induce some sort of tuberculosis (*M. xenopi* and *M. scrofulaceum* are usually non-pathogenic) was added *M. leprae*, which had been armadillo-grown, and purchased under the form of lepromin.

About 15 mg of proteins liberated from the cytoplasm of each of these bacteria in 1 ml buffer (CaCl$_2$ - 0.04M; Mg-acetate - 0.015M; Tris-HCl - 0.02M; ph - 7.4) were treated for 10' at 37° C. with 10 units of RNase, then immediately chromatographed twice on a Sepharose 6B column and the A60 antigens from the 6 starting Mycobacteria were brought therewith to immunochemical purity. Samples applied to the column were 1 ml, bed volume of Sepharose was 10 ml and void volume was 3.5 ml.

The several A60 antigen products extracted from these 6 Mycobacteria were recognized by their characteristic immunoelectrophoretic behavior, as specified above. All Mycobacterial species analyzed contained this antigen in large quantities. The A60 antigen of *M. leprae* was recognized to be the principal antigen of lepromin, also named A 7 in former reference systems.

The production of polyclonal murine antibodies against the isolated A60 antigens was carried out according to known procedures. Such procedures include recovery from the serum of peritoneal cavity of animals inoculated with the antigen. Briefly, Balb/c mice were primed with Pristane (0.50 ml I.P.). Fifteen days later, one ml of a 10% suspension of an aqueous solution of the antigen (10 mg/ml) in Freund incomplete adjuvant was inoculated intraperitoneally. After 15 days, 2 weekly intraperitoneal re-inoculations took place. The mice produced therewith an ascites that secreted large amounts of antibodies. The mice were punctured and drained every 3 days, and they usually died after the 5th to 6th drainage, from dehydration.

Monoclonal antibodies were obtained in Balb/c mice according to known procedures. (Köhler, G. and Milstein C.: Continuous cultures of fused cells secreting antibody of predefined specificity. Nature, 1975, 256, 495–497).

Fifty-one clones each secreting an antibody specific against the A60 antigen derived from *M. bovis* strain BCG were isolated, and three to six clones for each of the five other isolated A60 antigens.

Polyclonal antibodies are a heterogenous population of antibodies directed against all epitopes available in an antigen. A monoclonal antibody is a homogenous population of antibodies directed against one single epitope of an antigen. This epitope may or may not be shared by other homologous antigens. In the present case, a monoclonal antibody may be specific for a Mycobacterial strain, subspecies, species, genus.

The availability of polyclonal antibodies, of monoclonal anti-bodies and of a large supply of A60 antigens/(except *M. leprae*) of high purity isolated as described above allowed the development of several diagnostic tests. Their use will be exemplified in the following examples:

EXAMPLE I

120 µg of antigen-like A60 in 120 µl phosphate buffered saline, pH 7.2 (PBS) were incubated with 3 µl of I 125 (300 µCi) and 10 µl of chloramine T (6.5 mg/ml in phosphate buffered saline pH 7.2) during 3 minutes at 20° C. The reaction was stopped by addition of 10 µl sodium metabisulfite (8.45 mg/ml in phosphate buffered saline pH 7.2). The final volume was brought to 200 µl with PBS and chromatographed on 2 ml of Sepharose 6B. The exclusion peak containing I 125 labeled A60 antigen was stored in the presence of 0.2% albumin and 0.02% NaN$_3$.

A radioimmunological (RIA) test was therewith developed for the determination of minimal amounts of antibodies. Protein A from *Staphylococcus aureus* was purchased from Pharmacia (Uppsala, Sweden). This protein has the property to specifically combine with human and mouse IgG even if antigen is bound to them. The protein A was adsorbed on the walls of polystyrene tubes. I 125 labeled A60 antigen (about 3000 CMP per µl) was added to unknown amounts of antibodies and the resulting complex was thereafter contacted with the protein A carrier. After suitable incubation allowing attachment of the anibodies to the protein A, the amount of radioactivity attached to the walls of the polystyrene was measured.

This classical radioimmunological assay (RIA) test repeated with the various polyclonal antibodies and the 6 labeled A60 antigen products available established that all polyclonal antibodies obtained by the injection of these antigens as vaccines interreacted to a large extent (7% to 100%) with all A60 labeled antigen products applied in an RIA test.

It was discovered from further tests that the radioactive labeled A60 antigens competed to a variable extent with Purified Protein Derivative (PPD) which is a purified preparation of tuberculin (i.e., an extract of BCG), and surprisingly also with lepromin (an extract of *M. leprae*) and with Leoprosy-derived-corynebacteria (L.D.C.), for complexing with the 6 polyclonal antibodies tested.

This indicates that A60 antigens of various Mycobacteria species, including those that do not provoke tuberculosis, contain at least one epitope common to all species composing the CMN super-group and against which antibodies are made. An exploration of the specificity of the various monoclonal antibodies obtained was also made by the were found to be overlapping to some extent. However, one clone secreting an antibody absolutely specific for A60 antigen of *M. kansasii* and for A60 like antigen of *M. scrofulaceum* could be isolated as well as four (out of 51 clones) for A60 antigen of *M. bovis*. On the other hand, clone 31 was found to secrete antibodies that reacted with all A60 antigens presented. It had a very large spectrum of immunological activity. No clones secreting antibodies specific for the other Mycobacteria species were obtained, no doubt because the initial number of antibody secreting clones isolated was too small.

EXAMPLE II

The A60 antigen of *M. bovis* was adsorbed to the walls of polystyrene microcups (96 per plate) at pH 9.6 in 0.1M carbonate buffer. After adsorption, the wells were filled with a solution of 0.1% in albumin in phosphate buffered saline at 4° C. during 18 h, then the wells were washed with an 0.05% Tween 20 solution in PBS and the wells were finally drained and stored dry in the cold (4° C.). It was found that the A60 antigen adsorbed to the walls and kept dry could be stored at 4° C. during at least 4 months without any observable degradation in its immunological properties.

Goat antibodies against human IgG were purified by affinity chromatography and labeled with peroxidase following classical procedures. This reagent has the dual function to adsorb to human IgG through its antibody moiety and to allow a colored enzymatic reaction through its peroxidase moiety.

An enzymo-immunoassay (EIA) was thereby prepared, where human antibodies against A60 antigen contained in a test sample, e.g., patient sera, were specifically adsorbed on the sensitized walls of the microcup by complexing with the adsorbed A60 antigen. After washing with TweenPBS, the presence of the human specific antibodies that attach to the A60 antigen on the wells is revealed by peroxidase-labeled anti-human IgG antibodies. These antibodies will attach to any human IgG present, and after washing, the presence of these antibodies is analyzed by a color reaction based on the enzymatic activity of its peroxidase moiety.

As a parallel test, the same A60 antigen (500 μg/ml) was adsorbed to 20% suspension of latex particles (0.8μ in diameter) in 0.1 m glycine buffer at pH 8.0. After washing the latex particles, verification that agglutination would take place in the presence of a dilution of anti-A60 antiserum in PBS was accomplished by mixture of 50 μl of a dilution of a polyclonal antibody on a slide. After 5 minutes of slow rotation, the limit of dilution of the antibody was recognized to be 1/1200. Competition between the sensitized latex and free A60 antigen for this dilution of antibody showed that 2.6 μg/ml of free A60 antigen were needed to inhibit the latex agglutination induced by the diluted antibody.

These two qualitative tests were used to verify the presence of antibodies against A60 antigen in the sera of patients who were known to be positive for tuberculosis according to a standard cutaneous test. In order to avoid non-specific reactions of the sera with the latex sensitized with A60 antigen, the sera had to be diluted 6 times in PBS before use.

A correlation of 98% was found for positive reactions between cutaneous tests and EIA results just described. Sera shown to be negative by the standard tuberculin test proved negative by this EIA, although the EIA did produce some false positives (97% correct).

The rapid latex slide agglutination test was normally slightly less sensitive. It picked up only 94% of the positives. However, all cutaneous negatives were also negative with the slide test.

These results indicate that antibodies against the A60 antigens of the invention derived from Mycobacteria are present in large quantities in the serum of patients that showed positive for tuberculosis in a cutaneous tuberculin test and that diagnostic tests—latex agglutination or EIA—based on recognition of such antibodies in serum by the A60 antigen of the invention are valuable diagnostic tools.

EXAMPLE III

Several proteases are available to the art in order to break proteins into fragments. The most popular enzymes used for this purpose are trypsin, papain, chymotrypsin and subtilisin, but more esoteric enzymes may be applied as well as chemicals such as CNBr and beta-propiolactone. They split the protein at various specific aminoacid junctions producing thereby different fragments. Experiments were conducted to verify that the splitting with trypsin does not occur precisely at an immunologically important epitopic site. This was done by treating A60 antigen of *M. bovis* with the protease, and verifying therefore the ability of the fragments to compete for *M. bovis* antibodies with I 125 labeled antigen in an RIA-test, as in Example I.

Here, trypsin was suitable and no additional protease was used.

A60 antigen of *M. bovis* (15 mg in 15 ml) was treated with trypsin according to known procedures. Briefly, trypsin attached to cellulose via CNBr was incubated with the solutions of A60 antigen in a buffer constituted of Hank's solution at pH 7.2. After 3 hours at 37° C., the cellulose-bound trypsin was removed by centrifugation.

The solution of degraded A60 antigen of *M. bovis* was dialysed against an 0.1M glycine buffer at pH 8.0, then contacted with latex particles (0.8$\mu$ in diameter) as in Example II. A latex agglutination test was thereby produced that provided identical in sensitivity to a test developed with the intact A60-like antigen. Its superiority resided in the fact that the tendency to spontaneous unspecific aggregation of the latex particles in the presence of serum components was substantially reduced.

EXAMPLE IV

The presence of Mycobacteria in the sputum of diseased people can be assessed by mixing the sputum with fluorescently-tagged antibodies developed against A60 antigen on a microscope slide. After suitable incubation, the slide is washed, is mounted and is viewed in a fluorescent microscope. This diagnostic test is too sophisticated to be applied in those geographic areas where the disease is most common; i.e., Spain, Southern Italy, North Africa.

A less sophisticated test for such bacteria can be carried out as follows: Latex at a concentration of 10% and pH 8.1 was incubated during 72 h at 45° C. with MAb 31, obtained after cloning a hybridoma secreting antibodies against *M. bovis* A60 antigen. After washing, the latex suspension was assayed in a direct aggregation test for the presence of Mycobacteria in sputum. *Mycobacteria bovis* were mixed at various levels of concentration with the sputum of a disease-free donor to provide standardized test samples of known concentration and the resultant fluids appropriately diluted 1:5 with phosphate buffered saliva at pH 7.5 were mixed with the sensitized latex. Slow rotation was induced by hand during 3 minutes, after which the degree of aggregation of the sensitized latex was read under incident light. The test was not very sensitive.

The presence of at least 100,000 bacteria/ml sputum was needed to begin to see an aggregation. Nevertheless, despite its insensitivity, the test was functional, and no less sensitive than direct microscopic observation of smears.

A more sensitive detection system for the presence of the bacteria was obtained through an EIA, where MAb 31 obtained as above was adsorbed onto the walls of polystyrene wells as in Example II. After incubation of the diluted sputum into the wells, these were washed and the presence of bacteria attached to the MAb 31 antibody was revealed by incubation of the wells with a peroxidase-labeled second antibody and coloration with O-phenylene diamine, as in Example II. In this test, the sensitivity was increased and the presence of 10,000 or even less bacteria/ml could be detected.

It was also found that in case ribosomes and ribosomal RNA contaminate the A60 antigen prepared from the bacteria cytoplasm; a treatment of the extract with RNAse and DNAse prior to exclusion chromatography considerably improved the purity of the chromatographed product. Sepharose 4B or other molecular sieve material may be as efficient as Sepharose 6B for the separation of A60 antigen from other cytoplasmic constituents. Immunologically active fragments of A60 may be isolated in ways other than affinity chromatography. Other enzymes than trypsin may prove more efficient in the obtention of the immunologically active fragments.

The isolation of the A60 antigen and its use in diagnostic tests designed to detect in simple and easy to perform fashion the presence of antibodies against Mycobacteria, including both IgG and IgM specific antibodies as claimed in U.S. application Ser. No. 678,170, has made possible additional discoveries.

Cellular Immune Reaction From A60 Antigen

The capacity of A60 antigen isolated from strain BCG to induce delayed hypersensitivity reactions were explored by the measurement of the footpad swelling of primed mice. Six-weeks old NMRI female mice were primed by the subcutaneous injection of 75 μl aliquots of a water-in-oil emulsion (F.I.A.) containing 1.5 μg/animal of either A60 antigen at a dose 1.5 μg/animal or tuberculin lot 80 C 12, used undiluted as received from the manufacturer.

Reactions indicative of delayed hypersensitivity were elicited by injections as challenge antigen of 30 μg of A60 antigen solubilized in phosphate buffered saline or the same amount of pure tuberculin lot 80 C 12 used undiluted, into hind footpads of the primed animals. After 24 hours, the pad thickness was measured by a caliper. Table I resumes the results obtained. Eight mice were used per experimental group:

TABLE I

Delayed Hypersensitivity Reactions

| Injection | Challenge | Mean footpad swelling in mm |
|---|---|---|
| A 60 | A 60 | 1.62 |
| Tub 80 C 12 | Tub 80 C 12 | 1.40 |
| Buffer | A 60 | 0.11 |
| A 60 | Buffer | 0.04 |
| F.I.A. alone | A 60 | 0.01 |
| Tub 80 C 12 | A 60 | 1.34 |
| A 60 | Tub 80 C 12 | 1.49 |

Clearly, the A60 antigen elicits an hypersensitivity reaction similar to the one observed when tuberculin is used.

The discovery that A60 antigen is a potent immunogen eliciting cellular immune responses prompted the investigation of the value of A60 antigen as a replacement for conventional "tuberculins" in cutaneous testing for tuberculosis and its use as a quality control standard for comparing various commercial tuberculin preparations.

A60 Antigen Used As Tuberculin

The suitability of A60 antigen isolated from BCG as a challenge antigen similar to conventional "tuberculins" of various types was first investigated by means of a classical "tuberculin" evaluation test.

Guinea pigs (400 gr. to 600 gr.) were sensitized with 0.1 μg of killed *M. bovis,* administered intramuscularly. Four weeks later, various doses of A60 antigen were inoculated intradermally on the shaved animals' sides. A hypersensitive reaction was indicated by an indurated area or wheal which was measured in diameter after another 24 hours.

The results of this experiment are given in a graph reproduced in FIG. 3. The minimal dose at which an established hypersensitivity was manifested or indicated was found to be 15.0 nanograms A60 antigen. This experiment demonstrates that a challenge of *M. bovis* primed animals may be accomplished with A60 antigen in lieu of tuberculin.

ELISA Analysis of Non-Homogeneity of Commercial "Tuberculins"

The quality in terms of degree of homogeneity of five commercial preparations or lots of "tuberculins" were analyzed in an enzyme-immunoassay. The tuberculins were diluted 1:10 and 1:100 in carbonate buffer (0,01M, ph9,6) and absorbed in the presence of glutaraldehyde (0,030M concentration) on the wells of a microtiter plate to serve as the capture antigen for the development of an enzyme-immunological test. Mouse antibodies against A60 antigen at various dilutions were applied and the presence of these antibodies in complexed form on the plate was revealed by a peroxidase-labelled antimouse IgG (Dako, Denmark) and subsequent color development with ortho-phenylene diamine and $H_2O_2$ in citric-phosphate buffer pH 5,3. The results are given in Table 2.

TABLE II

Optical density at 492 nm of a mouse-enzyme-immunological dosage with five commercial lots of tuberculins used as capture antigen.

| | Anti-A60- antigen mouse antiserum dilution | | |
|---|---|---|---|
| Tuberculin Lot | 1:1,000 | 1:5,000 | 1:10,000 |
| 86 A 20 | | | |
| Pure | 1.05 | 0.30 | 0.19 |

TABLE II-continued

Optical density at 492 nm of a mouse-enzyme-immunological dosage with five commercial lots of tuberculins used as capture antigen.

| Tuberculin Lot | Anti-A60- antigen mouse antiserum dilution | | |
|---|---|---|---|
| | 1:1,000 | 1:5,000 | 1:10,000 |
| 1:10 | 1.03 | 0.31 | 0.20 |
| 1:100 | 0.65 | 0.23 | 0.15 |
| 84 H 30 | | | |
| Pure | 0.41 | 0.18 | 0.13 |
| 1:10 | 1.31 | 0.47 | 0.28 |
| 1:100 | 1.28 | 0.47 | 0.28 |
| 83 I 26 | | | |
| Pure | 0.35 | 0.19 | 0.14 |
| 1:10 | 1.05 | 0.51 | 0.36 |
| 1:100 | 1.39 | 0.42 | 0.29 |
| 85 K 28 | | | |
| Pure | 0.98 | 0.40 | 0.27 |
| 1:10 | 1.04 | 0.46 | 0.39 |
| 1:100 | 1.03 | 0.51 | 0.42 |
| 80 C 12 | | | |
| Pure | 0.84 | 0.23 | 0.17 |
| 1:10 | 1.01 | 0.29 | 0.19 |
| 1:100 | 0.86 | 0.28 | 0.19 |

An examination of the data leads to the following conclusions:

1. The tuberculins when used in pure form as sensitizing material inhibit the enzyme-immunological reaction in three cases since the optical density values obtained with them is substantially lower than those obtained when the tuberculins are applied at a 1:10 or even 1:100 dilution. The inhibiting effect is best observed when the mouse anti-A60 antigen antibodies are given in a concentrated form (1:1.000 dilution) but the effect is still observable at higher dilutions. Presumably, the immunologically reactive material effective for sensitization of the solid phase is overshadowed by competing contaminants in three out of the five lots tested.

2. The degree of contamination varies for different tuberculin lots since the inhibiting effect is nonexistent for lot 86 A 20, is slight for lot 80 C 12, is more accentuated for lot 85 K 28, is very pronounced for lot 84 H 30 and is maximal for lot 83 I 26.

3. The potency relative to antibodies against A60 antigen of the different lots of tuberculin is unequal. This is observed when a low concentration of sensitizing or capture antigen is used (e.g., a 1:100 dilution of antigen) and also when diluted antibodies are applied (i.e., a 1:5,000 and 1:10,000 dilution of mouse anti-A60 antigen antibodies).

Lot 85 K 28 is more potent than the other analyzed lots and lot 86 A 20 is the weakest.

Dosage of A60 Antigen

The same experimental evaluation was applied to A60 antigen isolated from BCG. In this case, the availability of pure material allows the quantification of the amount of sensitizing antigen used. Solutions ranging from 10 µg to 5 ng A60 protein per ml were applied. Table 3 records the results obtained.

TABLE III

| A60-like antigen concentration | Anti-A60-like antigen mouse antiserum dilution | | |
|---|---|---|---|
| | 1:1,000 | 1:5,000 | 1:10,000 |
| 10 ug | 2 | 1.49 | 0.85 |
| 5 ug | 2 | 1.48 | 0.86 |
| 0.5 ug | 2 | 1.38 | 0.81 |
| 0.05 ug | 1.47 | 0.68 | 0.32 |
| 0.005 ug | 0.42 | 0.29 | 0.18 |

(1) Contrary to most lots of tuberculins assayed, large doses of the sensitizing A60 antigen show no inhibiting or competitive effect on the E.I.Assay.

(2) Saturating amounts of the A60 sensitizing antigen seem to be attained when 0.5 µg or more are used, since the sensitivity of the system is not improved with higher concentrations as observed when high dilutions (1:5,000 and 1:10,000) of the anti-A60 mouse antibodies are applied.

(3) The intensity of the observed responses is much greater than that observed for the lots of tuberculins analyzed.

The determination of the potency of a given tuberculin preparation with respect to A60 antigen is thus possible.

One scheme consists in a competition assay where an enzyme-labelled or radioactivity-labelled A60 antigen competes with the antigen contained in the tuberculin preparation for a limited amount of anti-A60 antigen antibody attached on a solid phase, such as the wells of a microtiter plate. The antibody may be monoclonal.

However, the information and materials at hand pointed to the development of an indirect non-competitive test based on an enzyme-labelled anti-mouse antiserum (after U.S. Pat. No. 4,298,687).

Serial dilutions of A60 antigen ranging from 0 to 500 nanograms were made and incubated (0.1 ml) for 3 hours at 37° C. in the presence of 0.1 ml of mouse antiserum against A60 antigen diluted to a 1:5,000 level (final dilution.).

The solutions (0.2 ml) were thereafter incubated for 18 hours (overnight) at room temperature in microtiter wells coated with 500 nanograms of A60 antigen. The wells were washed, an excess of peroxidase-labelled anti-mouse antiserum (Dako, Denmark) was added and incubation was continued for three more hours at room temperature. After washing, the presence of peroxidase was manifested by color development with ortho-phenylene diamine and $H_2O_2$ in citric acid-phosphate buffer.

In this detection system, maximum color development occurs when A60 antigen is absent from the reacting fluid and minimum color development near that of the background is obtained when an amount of A60 antigen sufficient to bind the totality of the antibodies against A60 antigen with the color development intensity varying between the limiting levels in accordance with the amount of A60 antigen between these extremes. Thus, a reference curve based on varying color development levels can be constructed of A60 antigen concentration in unknown fluids and a monoclonal antibody can also be employed for this purpose.

In this way, the same five lots of commercial tuberculins were analyzed at a 1:100 dilution. Their content in A60 material reflected quite accurately the results obtained in Table II. Most potent was lot 85 K 28 (7 µg A60 antigen equivalent/ml) and least concentrated in A60 materials was lot 86 A 20 (0.6 µg A60 antigen equivalent).

Antigen 60 Interspecificity

The availability of a refined detection system for the serology of Mycobacterial infections permitted the investigation of its applicability in several other Mycobacterial infections. Very unexpectedly, it was found that the A60 antigen is a potent interspecific antigen that reacts with the sera of patients suffering from a variety of Mycobacterial infections, so that the serum from a subject positively identified as infected with tuberculosis will be determined equally positive if A60 antigen isolated from Mycobacterial species other than *M. bovis* are used as capture antigen. As a convenient example, A60 antigen isolated by the procedure of the prior application from *M. paratuberculosis, M. avium* or *M. smegmatis* may be used instead of A60 antigen isolated from *M. bovis* for the serodiagnosis of tuberculosis in subjects either human or animal. Sera from five *M. avium* infected patients were obtained from the Cleveland Metropolitan General Hospital (U.S.A.). All five gave positive results in a serodiagnosis test with A60 antigen from *M. bovis* and also A60 antigen from *M. avium* and *M. paratuberculosis.* Sera originating from patients infected with *M. xenopi* were immunologically reactive with A60 antigen isolated from *M. bovis,* as were sera from *M. kansassii* infected patients with A60 antigen isolated from *M. bovis.*

Bovine sera originating from animals infected with *M. bovis* and others with *M. paratuberculosis* were immunologically reactive in the same way in tests where the capture antigen was A60 antigen from *M. bovis* strain BCG or *M. paratuberculosis* or *M. avium.*

As regards the utility of the A60 antigen as a challenge antigen for providing a visible manifestation of an established hypersensitivity in the test subject, it should be noted that the Pharmacopoea requires that such test preparations produce a delayed hypersensitivity reaction, i.e., a swelling or wheal, at a test dosage which when multiplied 100 fold itself imparts no acquired sensitivity against the test antigen. That is to say, an acceptable test antigen must exhibit a "safety factor" exceeding 100 times between its so-called "revealing dose", i.e., that amount at which a cellular response indicative of an established sensitivity to the antigen in the test subject, and the amount that will be sufficient to provoke a strong humoral response yielding effective levels of circulating antibodies as normally corresponds with immunization. Tests have established that the present A60 antigen fully satisfies this requirement, particularly since its minimum revealing dose is extremely small as already established above.

From what has already been said, it will be understood that the hypersensitivity manifestation or indication given by the present A60 antigen will not be confined to tuberculosis but will extend also to various other infections originating from Mycobacteria, including leprosy. This lack of specificity may under some circumstances be perceived as an advantage rather than a disadvantage for example when used for screening tests in less developed countries where a generalized discrimination of Mycobacterial infections in the test population might constitute important medical information in its own right. If a high degree of specificity for the identification of a specific Mycobacterial infection is required, this can be generally obtained by appropriate definition of the discrimination point between a positive or negative conclusion, as is indeed already practiced for known commercial "tuberculin" preparations. That is to say, the degree of the manifestation of sensitivity varies with different infections of the group in question so that as a practical matter, tuberculosis can be distinguished from other Mycobacterial infections, especially that attributable to *M. avium* by a significantly greater area of swelling or induration at the test site so that a positive diagnosis for tuberculosis can readily be based on this increased diameter of the swelling due to the sensitivity reaction.

As a rule, the presence of a hypersensitivity reaction or test swelling will occur within a relatively short time and usually 24–48 hours between the time of administration of the test dose of the antigen and observation of the test site for the usual test responses of swelling, inflammation and the like.

It will be appreciated that the A60 antigen of the invention is characterized by important advantages compared with previously known antigens derived from Mycobacteria and especially those associated with tuberculosis. As the comparative data provided above shows, typical commercially available tuberculin preparations exhibit a remarkable variation in their immunological activity that denotes a degree of nonhomogeneity that is quite unexpected for commercial test preparations. In contrast, the present antigen material has been found to exhibit quite uniform immunological activity, a number of different batches of the present antigen having now been prepared over time and all found to behave in essentially identical respects. Furthermore, a standard reference unit for the A60 antigen can be quantified by an objective reproducible spectrophotometric procedure described above that does not depend upon subjective considerations as is true of the current standardization tests for commercial tuberculosis which depend upon the personal observation of the extent of a cutaneous sensitivity reaction.

While quite specific molecular weight fractions derived from tubercular bacilli have been proposed and are presumably of uniform composition, they are necessarily only recovered in very small amounts and by rather complicated purification techniques. In contrast, the A60 antigen is recovered in usefully large volume from the starting material by a relatively simple procedure. Moreover, the electrophoretic reference system developed by Closs for classifying the various antigens contained in products derived from tubercular bacilli and like organisms provides a readily available way of analyzing the purity and homogeneity of the products of this invention. These products have the virtue of a useful heat stability, being essentially unaffected by heating up to a temperature of about 100° C. Commercial tuberculins in contrast normally contain contaminants, including hydrolytic enzymes and may hence by pyrogenic.

What is claimed is:

1. An interspecific antigen of Mycobacteria consisting essentially of a mixture in substantially immunochemically pure form of a protein having a molecular weight of at least $4\times10^6$ Daltons and polysaccharide having a molecular weight of at least about $1\times10^6$ Daltons, and having when subjected to cross-electrophoresis an immunoelectrophoretic precipitation pattern corresponding to A60 antigen of *Mycobacteria bovis* strain BCG.

2. A method of detecting the prior exposure of a subject to Mycobacterial infections which comprises the step of injecting said subject intradermally or cutaneously with an effective amount of the antigen of claim 1 and after passage of a sufficient amount of time for the development by said subject of a hypersensitivity reaction, observing the site of said injection for the presence of significant induration as a positive indication of said prior exposure.

3. The method of detecting the presence of Mycobacteria in the humoral fluids of a subject which comprises mixing a sample of said humoral fluid with an antibody against the antigen of claim 1 and detecting the occurrence of complexation said antibody of said antibody Mycobacteria in said fluid.

4. A method of eliciting an immunological response against the antigen of claim 1 which comprises administering to said subject an immunologically effective amount of the antigen of claim 1.

* * * * *